(12) United States Patent
Wu et al.

(10) Patent No.: US 9,721,337 B2
(45) Date of Patent: *Aug. 1, 2017

(54) DETECTING DEFECTS ON A WAFER USING DEFECT-SPECIFIC INFORMATION

(71) Applicant: KLA-Tencor Corporation, Milpitas, CA (US)

(72) Inventors: Kenong Wu, Davis, CA (US); Meng-Che Wu, Mountain View, CA (US); Lisheng Gao, Morgan Hill, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/944,130

(22) Filed: Nov. 17, 2015

(65) Prior Publication Data

US 2016/0071256 A1 Mar. 10, 2016

Related U.S. Application Data

(63) Continuation of application No. 13/652,377, filed on Oct. 15, 2012, now Pat. No. 9,189,844.

(51) Int. Cl.
*G06T 7/00* (2017.01)
*G01N 21/95* (2006.01)

(52) U.S. Cl.
CPC ......... *G06T 7/001* (2013.01); *G01N 21/9501* (2013.01); *G06T 2207/10061* (2013.01); *G06T 2207/30148* (2013.01)

(58) Field of Classification Search
CPC ....... G06T 7/0004; G06T 7/001; H01L 22/12; G01N 21/956; G01N 21/95607; G01N 21/9501
See application file for complete search history.

(56) References Cited

U.S. PATENT DOCUMENTS

| 6,336,082 | B1 | 1/2002 | Nguyen et al. ............... 702/179 |
| 6,553,329 | B2 | 4/2003 | Balachandran ............... 702/118 |
| 7,133,070 | B2 | 11/2006 | Wheeler et al. ........... 348/223.1 |
| 9,092,846 | B2 * | 7/2015 | Wu et al. ................ G06T 7/001 382/149 |
| 9,189,844 | B2 * | 11/2015 | Wu et al. ................ G06T 7/001 382/149 |
| 2005/0249318 | A1 | 11/2005 | Minemura ..................... 375/341 |
| 2006/0078192 | A1 | 4/2006 | Oh et al. ....................... 382/151 |
| 2006/0083135 | A1 | 4/2006 | Minemura ................. 369/47.51 |
| 2007/0230770 | A1 | 10/2007 | Kulkarni et al. ............. 382/149 |
| 2007/0288219 | A1 | 12/2007 | Zafar et al. ..................... 703/14 |
| 2008/0163140 | A1 | 7/2008 | Fouquet et al. .................. 716/4 |
| 2010/0076699 | A1 | 3/2010 | Auerbach ........................ 702/35 |
| 2011/0320149 | A1 | 12/2011 | Lee et al. ........................ 702/83 |

OTHER PUBLICATIONS

Supplementary European Search Report for EP 13 84 7706 mailed Apr. 29, 2016.

* cited by examiner

*Primary Examiner* — Andrew W Johns
(74) *Attorney, Agent, or Firm* — Ann Marie Mewherter

(57) ABSTRACT

Methods and systems for detecting defects on a wafer using defect-specific information are provided. One method includes acquiring information for a target on a wafer. The target includes a pattern of interest formed on the wafer and a known DOI occurring proximate to or in the pattern of interest. The information includes an image of the target on the wafer. The method also includes searching for target candidates on the wafer or another wafer. The target candidates include the pattern of interest. The target and target candidate locations are provided to defect detection. In addition, the method includes detecting the known DOI in the target candidates by identifying potential DOI locations in images of the target candidates and applying one or more detection parameters to images of the potential DOI locations.

23 Claims, 5 Drawing Sheets

DETECTING DEFECTS ON A WAFER USING DEFECT-SPECIFIC INFORMATION

BACKGROUND OF THE INVENTION

1. Field of the Invention

This invention generally relates to detecting defects on a wafer using defect-specific information.

2. Description of the Related Art

The following description and examples are not admitted to be prior art by virtue of their inclusion in this section.

Inspection processes are used at various steps during a semiconductor manufacturing process to detect defects on wafers. One important goal for any wafer inspection system is to suppress nuisance defects. Nuisance defects are those detected events which may not be relevant to semiconductor yields. These nuisance defects may be caused by wafer noise and system noise or are physical objects on the wafer. Nuisance defects may appear anywhere on a wafer. Some defects of interest (DOI) may appear at certain locations on a wafer. Context information for a DOI may be used as prior knowledge for defect detection. Several approaches that use context information have been developed to detect defects. One such approach uses graphical data stream (GDS) data or design information to find hot spots where defects may occur at a higher probability and to inspect defects around the hot spots. Another such approach matches defect background and keeps or removes matched defects after defect detection.

There are, however, a number of disadvantages to such approaches. For example, the first approach works with GDS data. However, GDS information may not be available in all circumstances such as for defect engineers in semiconductor fabrication plants. In addition, the user needs to do patch-to-design alignment (PDA) and run-time swath-based alignment to overlap care areas accurately on the images. If swath-based alignment fails, the locations covered by the swaths will not be inspected. The second approach, which is performed after defect detection, can significantly slow down inspection if the defect count and types of nuisance defects are relatively large. In addition, if the defect signal is relatively weak, huge amounts of nuisance defects may be detected. The defect signal may be defined as the maximum gray-level difference between an image with a defect and a reference image without the defect. The reference image is spatially-aligned with the defect image and may be acquired from neighboring dies or from multiple dies on the wafer. Furthermore, if the methods are performed for keeping systematic DOIs, other nuisance removal mechanisms are needed to separate nuisance defects and randomly-distributed DOIs. None of these approaches use defect-specific information.

Accordingly, it would be advantageous to develop methods and/or systems for detecting defects on wafers that do not have one or more of the disadvantages described above.

SUMMARY OF THE INVENTION

The following description of various embodiments is not to be construed in any way as limiting the subject matter of the appended claims.

One embodiment relates to a computer-implemented method for detecting defects on a wafer using defect-specific information. The method includes acquiring information for a target on a wafer. The target includes a pattern of interest (POI) formed on the wafer and a known defect of interest (DOI) occurring proximate to or in the POI. The information includes an image of the target on the wafer acquired by imaging the target on the wafer, a location of the POI on the wafer, a location of the known DOI relative to the POI, and one or more characteristics computed from the POI and the known DOI. The method also includes searching for target candidates that match the POI in a die on the wafer or on another wafer. The target candidates include the POI. POI search may be performed at a setup step prior to defect detection. After POI search, micro care areas (MCAs) may be created for each potential defect location. These locations may be provided for defect detection. In addition, the method includes detecting the known DOI in the target candidates by identifying potential DOI locations in images of the target candidates and applying one or more detection parameters to images of the potential DOI locations. Detecting the known DOI is performed using a computer system.

There are several differences between this method and currently used context-based inspection. First, this method does not rely on graphical data stream (GDS) data. In addition, a highly accurate care area alignment may be performed to detect specific defects. Furthermore, context and defect-specific information is used during setup and defect detection, not after defect detection.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a wafer. The system includes an inspection subsystem configured to acquire information for a target on a wafer. The target includes a POI formed on the wafer and a known DOI occurring proximate to or in the POI. The information includes an image of the target on the wafer acquired by imaging the target on the wafer. The inspection subsystem is also configured to search for target candidates that match the POI on the wafer or on another wafer and to acquire images of the target candidates. In addition, the system includes a computer system configured to detect the known DOI in the target candidates by identifying potential DOI locations in images of the target candidates and applying one or more detection parameters to images of the potential DOI locations. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
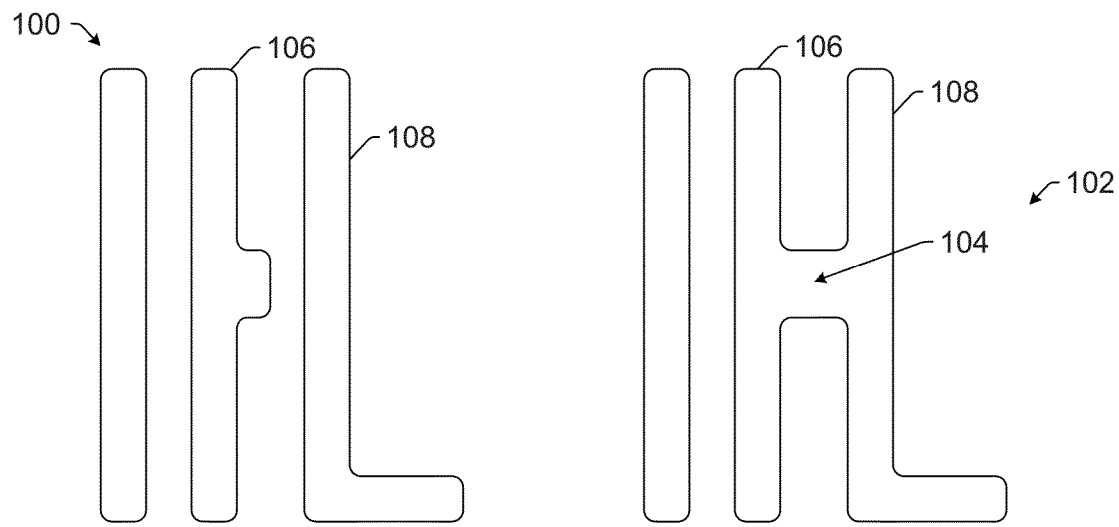
FIG. 1 is a schematic diagram illustrating a plan view of one embodiment of a pattern formed on a wafer and the pattern with a known defect of interest (DOI) detected in the pattern.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for detecting defects on a wafer. The method includes acquiring information for a target on a wafer. The target includes a pattern of interest (POI) formed on the wafer and a known defect of interest (DOI) occurring proximate to (near) or in the POI. The POI may include only a few patterned features in the entire design for dies formed or to be formed on the wafer. In other words, the POI included in the target does not include the entire pattern for a die formed or to be formed on the wafer.

Samples of DOI may be known from certain sources such as e-beam inspection or scanning electron microscopy (SEM) review performed on the wafer. In some such instances, the user will want to know the number of these kinds of defects on the whole wafer. Given the target information (sample DOIs in specific context), the embodiments described herein may be used to detect all DOIs and suppress the nuisance defects on the whole wafer. In addition, since the embodiments described herein are designed to detect defects in only target candidates containing certain patterns, the embodiments described herein are particularly useful for detecting systematic defects on wafers, which are defects that occur repeatedly in certain patterns on the wafers generally due to interactions between the pattern and the process used to form the pattern on the wafer. Therefore, the DOIs may include defects in the patterns formed on the wafer such as bridges.

In one such embodiment, as shown in FIG. 1, pattern 100 may be formed on a wafer and is shown in FIG. 1 as it might be imaged by a high-resolution inspection system such as an e-beam inspection system or an optical inspection system. The system may grab two images, one from the target location and the other from a die or wafer on which a POI search will be performed. The features shown in pattern 100 may be included in a target described herein since as shown in pattern 102, which is equivalent to pattern 100 but with a defect occurring therein, DOI 104 such as a bridging defect between patterned feature 106 and patterned feature 108 may have been detected in one or more instances of the pattern on a wafer. The patterns shown in FIG. 1 are not intended to represent any pattern that may actually be formed on a wafer. Instead, the patterns are intended to show what types of features may be included in the POI of the targets and the types of DOI that may occur therein. The number of patterned features included in the POI may be selected such that target candidates can be identified in images acquired for the wafer or other wafers with a predetermined accuracy. The size of the POI may be also determined as described further herein.

The information for the target includes an image of the POI on the wafer acquired by imaging the target on the wafer, a location of the POI on the wafer, a location of the known DOI relative to the POI, and one or more characteristics computed from the POI and the known DOI. In addition, the information for the target may include a location where the DOI may occur, and the location may be known and unique to the POI location. The information for the target may be generated during setup and may include identifying potential defect locations and computing defect information using test and reference images of sample defects.

In one embodiment, acquiring the information for the target includes importing locations of DOI samples. The sources of these locations may be obtained from inspection results and SEM review results. These locations may be used for grabbing images of the targets. In one embodiment, acquiring the information for the target includes displaying high-resolution images of DOI locations. The images may be generated from other systems such as SEM review machines or e-beam inspection machines. In addition, acquiring the information for the target may include providing a graphics user interface (GUI) to a user. The GUI may display any of the information that is acquired for the target.

In one embodiment, acquiring the information for the target includes grabbing the image of the target on the wafer in known locations of DOI using an inspection system. For example, during setup, the system grabs two sets of images, one from the target location in a die and the other from a die on which POI search will be performed. The set of images at the target location includes test and reference images. The system aligns one image to another and computes the difference of the two images. The user manually marks the DOI location and POI location by referencing to the test or difference image. The other set of images includes the test and reference images at the corresponding location in the die for POI search. The system automatically locates the POI location in the image of the die for POI search by correlating two reference images. A template, an image of the POI, may be grabbed from the die for POI search when the user specifies the POI location. Acquiring the information may also include defining the template location and size. In addition, acquiring the information may also include defining an area where one or more parameters may be determined for defect detection. The characteristics of POI and DOI may also be calculated. This target information will be saved for POI search which will be described later. In another embodiment, acquiring the information for the target includes grabbing images for all known DOIs in one die on the wafer or the other wafer in which searching for target candidates as described further herein will be performed. The locations of these templates may be obtained by correlating the images of the targets with the images generated from the die for POI search. There may be many types of targets. One template may be grabbed for each type.

In another embodiment, acquiring the information for the target includes specifying size, shape and location of care areas, size, shape and location of templates, and area where the one or more characteristics are determined in the images to which one or more detection parameters are applied (the images used for defect detection). Each of these steps may be performed as described further herein.

All templates may be grabbed from the same die for POI search. Due to relatively small variations in wafer structures, the image intensities of wafer patterns are sometimes substantially different across a wafer. This difference is referred to as color variation. Color variation is much smaller within a die than across a wafer. To ensure substantially high quality for POI search, all templates may be grabbed from one die and POI search may be performed on the die from which the templates are grabbed.

In one embodiment, acquiring the information for the target includes determining a similarity between a template and the image of the target and determining a uniqueness of the POI relative to other patterns proximate to the POI (i.e., the uniqueness of the POI with respect to its surroundings). For example, during template grabbing, a correlation value between images from the target die and the die for POI search may be calculated and saved for POI search. The template is selected to find the DOI location uniquely. A metric that measures uniqueness of the template may be calculated. For example, the ratio of the second highest peak and the highest peak values among correlation values for all locations in the image can be used as the uniqueness metric. The user can adjust the template location according to the uniqueness value.

Different targets can share some of the same target information. For example, two DOIs may be located in or proximate to the same POI. The potential locations for these two DOIs can be defined relative to the POI location and can be identified by searching for the POI. In another example, two DOIs have the same characteristics, such as polarity. A defect polarity is defined by its gray level, which is either brighter or darker than its background.

The method may also include searching all POI locations from one die to determine if a DOI is in or near any of the POI locations. The potential DOI locations corresponding to these POI locations are referred to as target candidates. In this manner, the method may include searching for all target candidates (or potential DOI locations) on a die. The same pattern occurs at these locations, but DOI may or may not occur at these locations. Only if a DOI is detected at a location are the pattern and the defect an actual target. In some embodiments, the method includes searching an image of a die on the wafer or the other wafer for the POI by determining if a template for the target correlates with different portions of the image of the die. For instance, an inspection system may be used to grab images for an entire die and run a correlation (such as a normalized cross correlation (NCC)) between the template and images to search for the POI locations. The locations passing a correlation threshold value are target candidates. The user has an option to refine target candidates manually. In one embodiment, the method includes creating a template for the POI and modifying the template by changing the size of the template or flipping, rotating, or processing the template. The template shape may be a square or rectangle and its size may be smaller than the image acquired by an inspection system. The POI locations obtained from POI search are saved and will be used during defect detection.

As semiconductor design rules shrink, there is a higher chance for certain wafer structures to cause a defect. When those wafer structures are identified using design data such as graphical data stream (GDS) data, the structures are generally referred to as "hot spots." More specifically, "hot spots" may be identified by using GDS data to determine which wafer structures may (hypothetically) cause defects on the wafers. There may be different types of hot spots in one die, and the same type of hot spots may be printed at multiple locations in a die. Defects produced at hot spots are generally systematic defects and usually have weaker signals than surrounding noise making them relatively difficult to detect.

Hot spots are therefore different than the targets described herein in that the targets described herein are not identified as wafer structures in GDS data that may cause defects. Instead, the targets are identified using one or more actual wafers on which the wafer structures have been formed. For example, e-beam inspection or e-beam review may be used to find targets in substantially local areas. Because the throughput of e-beam inspection and e-beam review is generally substantially low, it typically cannot be used to inspect an entire wafer. However, the embodiments described herein can be used to, given a location of a target such as one found by e-beam inspection, determine how many target candidates are formed on the entire wafer and how many DOIs appear at these target candidates. In this manner, given a sample defect location, the method may determine how many of this kind of defect are on the wafer.

The embodiments described herein are, therefore, substantially different than methods that detect defects using GDS-based inspection. For example, GDS-based methods try to catch any type of defect and perform patch-to-design alignment to generate images for run-time, swath-based alignment. In contrast, the methods described herein use an image of a sample DOI to find all defects of the same type on the entire wafer. The sample DOI can be from SEM review, e-beam inspection, or another inspection or defect review results file. During inspection, each POI location may be adjusted by correlating a template to the wafer image. Therefore, the two methods are not identical in that methods that use hot spots look for all possible defects while the methods described herein look for only specific known defects.

Figure 2:
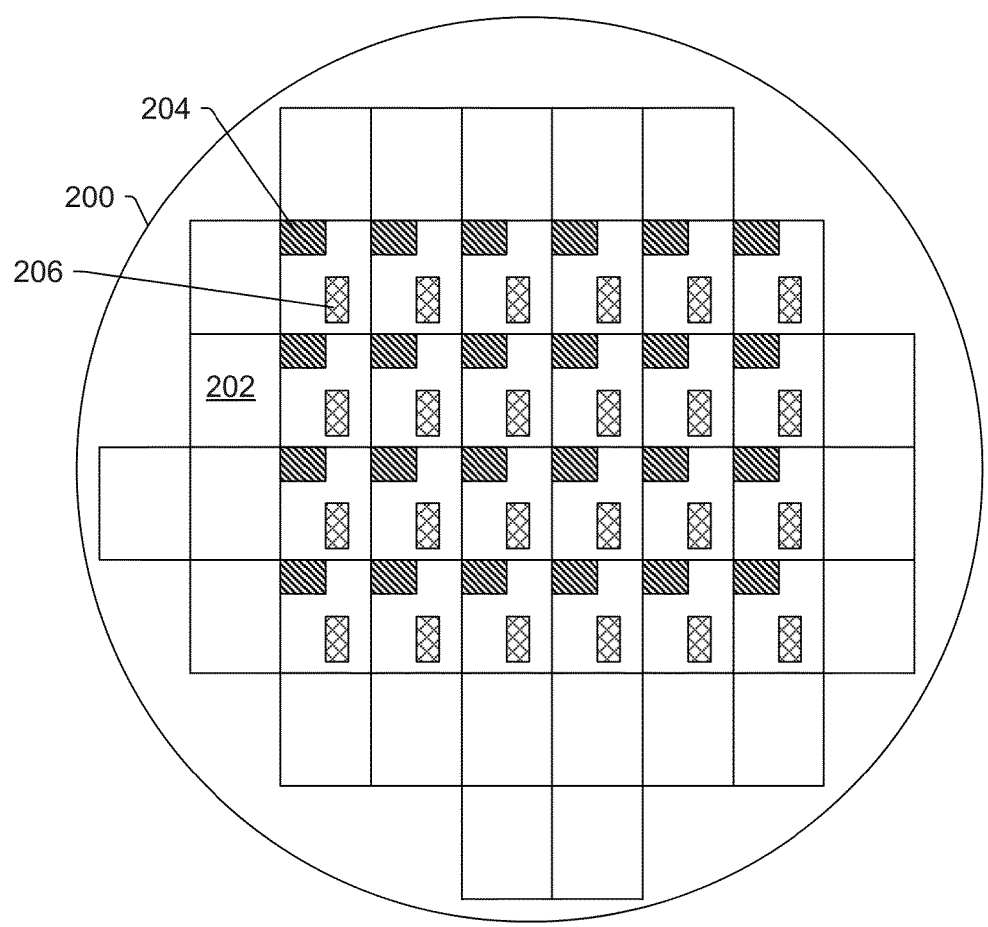
FIG. 2 is a schematic diagram illustrating a plan view of one embodiment of a wafer on which multiple dies and multiple patterns of interest (POIs) are formed within the multiple dies.

In one embodiment, the POI has a width and a height that are shorter than a width and a height, respectively, of dies formed on the wafer and the other wafer. For example, FIG. 2 shows a wafer on which multiple dies are formed and multiple POIs are formed within each of the multiple dies. In particular, wafer 200 may be printed during a wafer fabrication process (e.g., lithography) with dies 202 in a certain layout. A first POI 204 may be located in a first position in the dies. For example, first POI 204 may be located in the upper left hand corner of the dies. In addition, as shown in FIG. 2, POI 204 has a width that is less than a width of the dies and a height that is less than a height of the dies. A second POI 206 is located in a second position in the dies different than the first position of the first POI. Furthermore, as shown in FIG. 2, POIs 204 and 206 may have different dimensions from each other. For instance, since POIs 204 and 206 include different DOIs detected in different patterns, the two POIs may have different dimensions that are determined based on the DOIs located in the different patterns. In addition, as shown in FIG. 2, POIs 206 have a width that is less than a width of the dies and a height that is less than a height of the dies. Furthermore, POIs can be partially overlapped.

In another embodiment, the one or more characteristics include one or more characteristics of the known DOI. For example, defect information may be determined using test and reference images of sample defects. In particular, a reference image may be subtracted from a test image to generate a difference image, and the one or more characteristics of the known DOI may be determined from the difference image. In one such embodiment, the one or more characteristics include size, shape, intensity, contrast, or polarity of the known DOI. Defect size, shape, contrast, and polarity can be calculated using a difference image for the target. Intensity can be calculated from the test image of the target.

In one embodiment, the pattern included in the target is preferably resolvable by an inspection system. The embodiments described herein will not work in non-pattern areas and will not work for randomly distributed defects.

Setup of the methods described herein may also include any other suitable steps such as optics selection, which may be performed based on a known defect location. Some methods may also include inspecting any one target or one type of target with multiple optics modes of an inspection system. Optics modes are parameter configurations of wavelength, aperture, pixel size, focus, light level, and the like for inspection systems. Such a method may include selecting one or more parameters for the multiple modes. In this manner, the method may include setting up more than one mode for the target-based inspection. Such a method may include using the best mode for defect signal to select DOI from different dies and collecting target information from one die. Collecting the target information may include grabbing defect images at the die locations obtained in the first step and performing inter-mode image alignment to find the corresponding template in another mode that is best for POI search. The method may then include finding all target candidate locations in one die using the search mode. The locations can then be viewed or revised based on image patches grabbed at these locations. The detection recipe may then be setup with the best mode for defect signal. Inspecting the target candidates may be further performed as described herein.

The method also includes searching for target candidates on the wafer or on another wafer. The target candidates include locations of the POI (e.g., on an entire die). For example, there may be many locations with same type of pattern as a target. The same type of defect may occur at some of these locations. In order to detect all defects, these locations are searched and reported. A micro care area (MCA) may be defined around these locations as described further herein. A "care area" is a set of connected image pixels where defect detection is performed. For example, an MCA size of a location around the target may be defined by a user with the help of a computer graphics user interface (GUI). During inspection, these locations are examined for any DOI activity. To search these locations, the system may visit each pixel on the die and calculate a value for the similarity between the template and a pattern around the pixel on the die. If the similarity value is larger than a threshold defined at the template grab, the location of the pixel is marked as a POI location. The target candidate locations can be calculated by adding a position offset from POI to target candidate location. The image of the potential DOI location and POI location are grabbed and displayed to the user. The user can refine target candidates by reviewing images of POI and potential DOI locations and their similarity values. The POI locations are saved for defect detection. The target information and target candidate locations may be provided to defect detection.

In one embodiment, searching for the target candidates includes acquiring images for the target candidates using the best optics mode for image matching of the images of the target candidates to an image or a template for the POI. For example, POI searching may be performed with images obtained in an optics mode that is best for image matching. Acquiring target information and defect detection as described further herein may be performed using images obtained with a different optics mode. For example, in one embodiment, imaging the target on the wafer is performed using a first optics mode, and the images of the target candidates used for detecting the known DOI in the target candidates are acquired using a second optics mode different than the first optics mode. Inter-mode image alignment may be performed between two optics modes.

In one embodiment, acquiring the information for the target and searching for the target candidates are performed using an inspection system (i.e., the same inspection system). In addition, acquiring the target information and searching for the target candidates may be performed using an inspection system in a setup step before defect detection. For example, the same inspection system should be used for template grab and POI search. Alternatively, acquiring the information for the target and searching for the target candidates are performed using different inspection systems of the same type. In another embodiment, acquiring the information for the target and searching for the target candidates are performed in different dies, and searching for the target candidates is performed in one die using one or more templates for the target candidates.

In one embodiment, the target candidates can come from other sources, such as GDS-based pattern search. In these cases, the target-based inspection only needs to grab templates and compute the target information. Image-based search for POIs can be omitted. An MCA is created for each target candidate. During inspection, POI locations may be searched by correlating a template and the image generated for inspection. MCA locations may be corrected with the POI search result. Defect detection may be performed by the computer system within the MCAs.

Figure 2A:
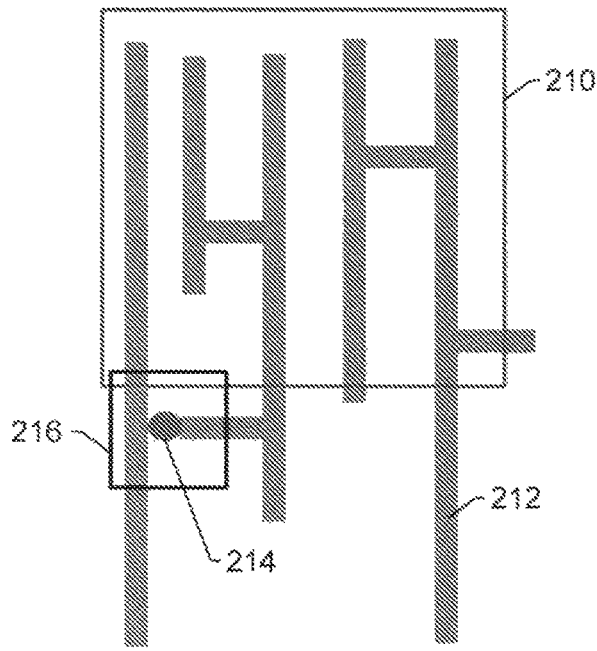
FIGS. 2a-2d are schematic diagrams illustrating plan views of different embodiments of a POI, one or more known DOIs occurring near or in the POI, and one or more micro care areas that may be generated for the known DOIs.
Figure 2B:
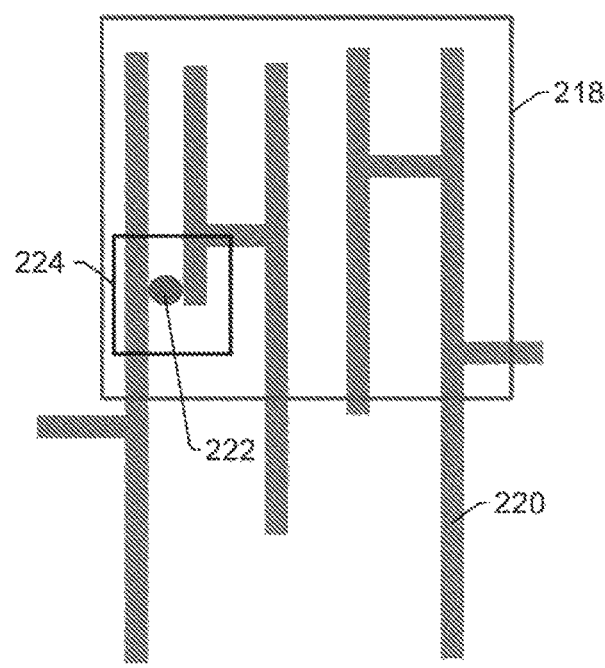
Figure 2C:
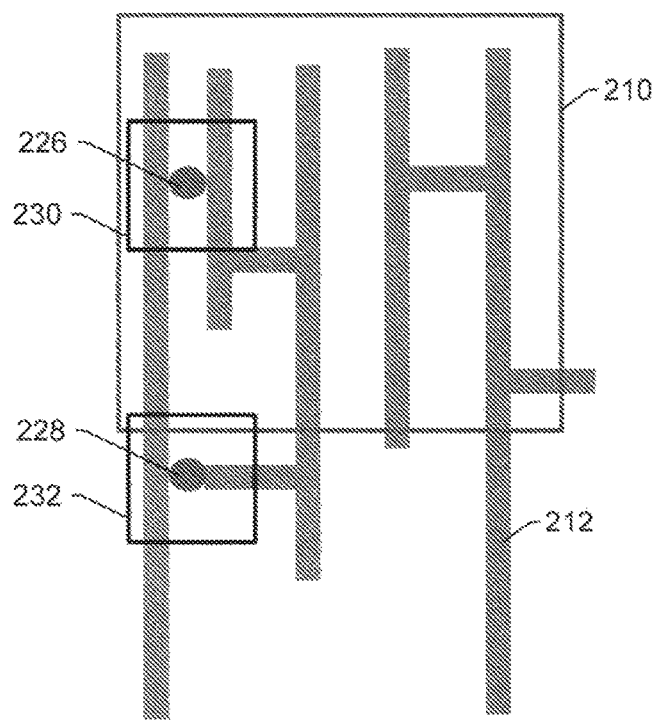
Figure 2D:
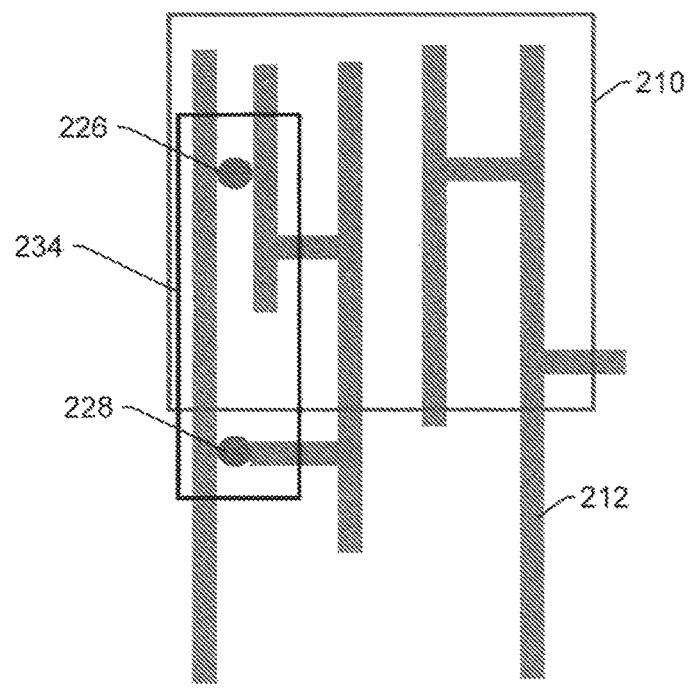

In one embodiment, the method includes determining one or more parameters of a care area for the target-based inspection. For example, for each type of defect, one type of MCA may be generated around the defect location based on a POI location. FIGS. 2a-2d show various relationships between a pattern on a wafer, a POI in the pattern, one or more DOIs located in and/or near the POI, and one or more MCAs that can be generated for each of the DOIs. For example, as shown in FIG. 2a, POI 210 may be located in pattern 212. The image of POI 210 shown in FIGS. 2a and 2c-2d is the POI as it may appear in a template for the POI. As shown in FIG. 2a, DOI 214 may be located near POI 210, but not necessarily in POI 210. MCA 216 may be positioned around and centered on the location of the DOI. In a similar manner, as shown in FIG. 2b, POI 218 may be located in pattern 220. The image of POI 218 shown in FIG. 2b is the POI as it may appear in a template for the POI. DOI 222 may be located in POI 218. MCA 224 may be determined around and centered on the location of the DOI. One POI can be associated with more than one DOI. For example, as shown in FIG. 2c, DOI 226 may be located in POI 210 while DOI 228 may be located near POI 210, but not necessarily in POI 210. MCA 230 may be positioned around and centered on the location of DOI 226, while MCA 232 may be positioned around and centered on the location of DOI 228. Therefore, each of the MCAs may be associated with only one of the DOI. However, an MCA may be associated with more than one DOI. For example, as shown in FIG. 2d, MCA 234 may be generated for both DOI 226 and 228. POI and MCA shapes are not limited to a square or rectangle. The patterns shown in FIGS. 2a-2d are not intended to represent any pattern that may actually be formed on a wafer.

In one embodiment, the method includes determining a care area location by correlating a template image for the POI and the images used for detecting the DOI. For example, POI search and defect detection may be two different wafer scans. The MCAs generated during POI search may serve as only approximate locations of defects during an inspection process. The exact defect locations can be identified by correlating the template with the image used for defect detection. In other words, the MCAs may not be accurately aligned with the potential defect locations. As such, during defect detection, a template may be correlated with the image to refine MCA location. Such an embodiment may also include correcting wafer stage uncertainty. Then, defect detection can be performed within these MCAs as described further herein. In this manner, target-based inspection may include only using image pixels in the care areas for the target candidates and as such, image pixels may not be used for non-target candidates on the wafer and inspection may not be performed for non-target candidates. Therefore, the embodiments described herein may be different than most inspection methods, which typically involve using image pixels for entire wafers or entire swaths on wafers that typically span an entire dimension on the wafers. Such currently used methods are advantageous for a number of use cases such as detecting any defects that might be present in any locations on the wafer. However, these methods may not be able to find any DOI if the wafer noise is substantially high and DOI signal is relatively weak. Since the embodiments described herein are performed for only specific DOI that are present in only specific target candidates on a wafer, the embodiments are capable of detecting DOI that have relatively low signal-to-noise ratios with substantially high throughput while substantially suppressing nuisance defects in other areas. In addition, if there is only one location for a specific DOI a POI search (setup step) can be bypassed.

In addition or alternatively to determining one or more parameters of a care area for the target, during setup the method may include identifying potential locations of target candidates on the wafer. For example, the position of the targets within a die that will be formed on the wafer and information about the layout of the dies on the wafer may be used to identify potential locations of the target candidates on the wafer and therefore potential locations of the DOI on the wafer.

The method further includes detecting the known DOI in the target candidates by identifying potential DOI locations in images of the target candidates and applying one or more detection parameters to the images of the potential DOI locations. The potential DOI locations may be proximate to locations of the POI. A POI may include 0 or more DOI locations, and POIs can be partially overlapped. In this manner, the method may include detecting other targets at the target candidate locations on the whole wafer.

Detecting the DOI may include identifying the exact locations of the target candidates and checking whether the known DOI exists at the locations based on the defect information. More specifically, during inspection, templates and defect information generated during setup may be sent to a computer system such as that described further herein. For example, in one embodiment, the detecting step includes providing the information for the target to a defect detection module such as a computer system described herein in order to identify the potential DOI locations accurately. In this manner, the template may be used to find the exact location of the target candidates. For example, in one embodiment, the detecting step includes identifying the potential DOI locations in the images of the target candidates by correlating a template obtained during setup and the images of the target candidates obtained during defect detection.

In this manner, the template may be correlated with the images acquired for the target candidates within a range using any suitable correlation such as NCC. This range is determined according to the wafer stage uncertainty and the inspection pixel size. A typical value is 20 pixels. The location of the pixel corresponding to the maximum NCC value is selected as the POI location. The target candidate location can be calculated based on the defect location relative to the POI location. In this manner, during inspection, the embodiments described herein find substantially accurate target candidate locations using image matching.

In the case where multiple POI locations of the same target appear in one image, POI search is performed for one location and the offset from the approximate MCA location to the true MCA location is calculated. This offset is applied to other approximate MCA locations in this image. It is not necessary to search for all POI locations.

MCAs can be generated to cover one or more of the potential DOI locations. For example, since the target candidate location is substantially accurate, an MCA can be defined around the location as described further herein. The size of the MCA can be, for example, 5 pixels by 5 pixels. Furthermore, since the embodiments described herein use defect specific information, DOI detection and nuisance suppression are more effective.

Since the embodiments described herein perform target-based alignment to substantially accurately locate all potential defect locations, the embodiments described herein are advantageous over swath alignment-based approaches which may be used in design-based methods. A swath is the raw image generated by a time delay integration (TDI) sensor that covers an entire die row. Swath-based alignment correlates the care areas to the swath. Swath-based alignment may fail for a relatively small percentage of the inspection data. If such misalignment happens, the whole swath will not be inspected or a substantial amount of nuisance defects will be detected and reported due to misaligned inspection data. However, the embodiments described herein will be immune to such alignment issues because the target-based correlations described herein are performed locally.

Applying one or more detection parameters to the images for the target candidates may be performed in any suitable manner. For example, in some embodiments, applying the one or more detection parameters includes generating difference images using the images of the potential DOI locations and a reference image, calculating a noise measure and a threshold, and applying a threshold to signals in the difference images. In another embodiment, the method includes determining one or more characteristics of difference images proximate to the potential DOI locations, and applying the one or more detection parameters includes applying a threshold to one or more values of the one or more characteristics of the difference images. The reference image may be, for example, an image of the potential DOI location in a die in which the DOI has not been detected, a median image of multiple dies, or a template acquired at setup. For example, in one embodiment, the images of the potential DOI locations to which the one or more detection parameters are applied include images generated using a reference image and a test image, and the reference image is a template for the POI. In this manner, the reference image may not be an image acquired during inspection. In other words, the reference image is not limited to an image acquired during inspection. In another example, a location of a non-defective target candidate may be identified on the wafer and an image may be acquired at the location on the wafer using the inspection system. This image may be subtracted from the image acquired at the location of another target candidate to generate a difference image, and a threshold such as that described herein may be applied to the difference image. Any signals in the difference image above the threshold may be identified as a defect or a potential defect. Detecting the known DOI is performed using a computer system, which may be configured as described further herein.

The method of using a template as the reference image is advantageous in certain situations. For example, if the number of systematic defects is substantially high, a majority of the dies on a wafer are defective. Therefore, it is substantially likely that a median of multi-die images is defective. Thus, the median image cannot be used as the reference image. The reference image may be determined at setup and verified as defect free. Therefore, it can be used during inspection.

In some embodiments, the method includes determining the one or more detection parameters based on the information for the target. For example, the one or more detection parameters (or the defect detection algorithm) may be noise adaptive. That is, if noise is relatively high in the images acquired for the target, the inspection sensitivity may be set relatively low. Otherwise, the inspection sensitivity may be set relatively high. The inspection sensitivity may be set relatively low by selecting a relatively high threshold that is applied to difference images for the target candidates. In contrast, the inspection sensitivity may be set relatively high by selecting a relatively low threshold that is applied to difference images for the target candidates. In addition, in another embodiment, the method includes determining the one or more detection parameters separately for each target type based on images for each target type, respectively. Therefore, since the methods can be used for different types of targets, different thresholds can be used for detecting defects in different types of target candidates. For instance, a first threshold may be used for detecting a first known DOI in a first type of target candidate, and a second, different threshold may be used for detecting a second, different known DOI in a second, different type of target candidate.

The same one or more detection parameters may be used to detect defects in each of the target candidates having the same target type. However, in another embodiment, the method includes determining the one or more detection parameters separately for each of the target candidates for which detecting the known DOI is performed based on the images of the target candidates, respectively. In this manner, the detection parameter(s) may be determined on a target candidate-by-target candidate basis. For example, once a potential target candidate or potential DOI location has been identified, the standard deviation of the difference image in a local area may be determined. The threshold may then be determined as: threshold=Mean+G+*Standard Deviation Of (difference in a local area), where Mean is the average value of the difference image in a local area and G and K are user-defined parameters. G and K are signed values. However, the threshold for each target candidate may be determined in any other suitable manner.

The DOI information may also be used to determine whether a known DOI exists at the potential DOI locations. For example, in an additional embodiment, the one or more characteristics include one or more characteristics of the known DOI such as any of those described above, and applying the one or more detection parameters includes applying a threshold to one or more values of the one or more characteristics determined from the images of the potential DOI locations. In one such example, if a characteristic of the known DOI such as polarity is consistent from DOI to DOI, then detecting the DOI may include thresholding the values for the characteristic. Such polarity-based thresholding can be applied to the image acquired for the target candidate that correlates to the template or a difference image generated as described above for the target candidate. Thresholding of the defect characteristic(s) may be used in combination with other thresholding described herein (e.g., thresholding the signals in the difference images). Using defect characteristics such as polarity and defect size in this manner can also be helpful for suppressing nuisance defect detection.

Figure 3:
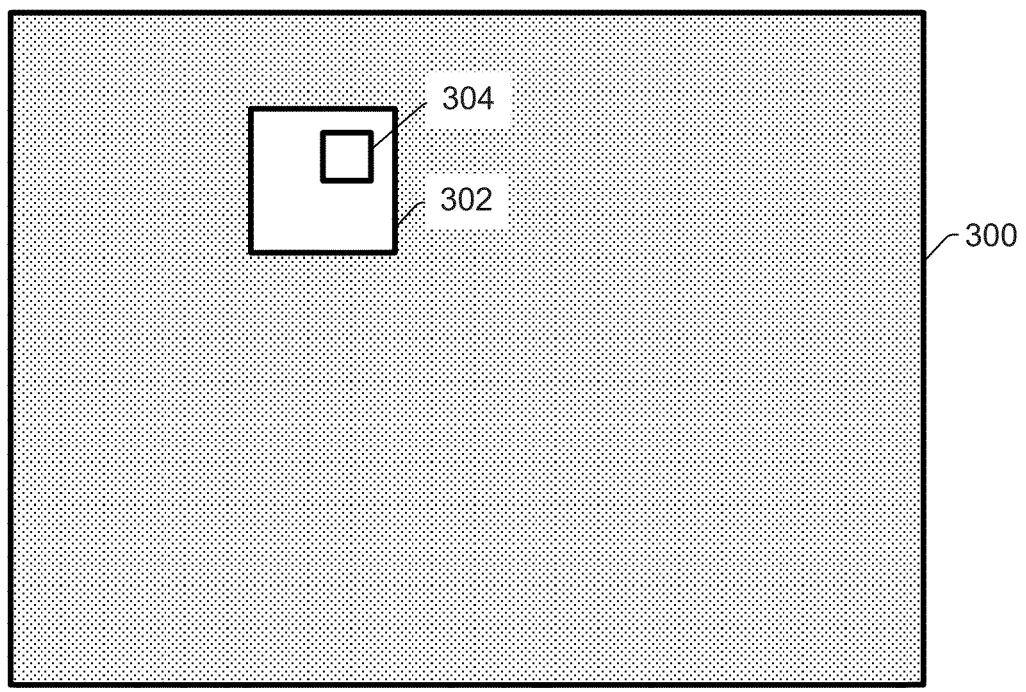
FIG. 3 is a schematic diagram illustrating a plan view of one embodiment of an image, an area within the image that is used to determine one or more detection parameters, and an area within the image to which the one or more detection parameters are applied.

In a further embodiment, the images of the potential DOI locations to which the one or more detection parameters are applied are images of care areas surrounding the potential DOI locations, and the care areas are determined based on a size of the known DOI occurring proximate to or in the POI. For example, the size of the image that is acquired at roughly the location of the target candidate may be relatively large to be sure that an image is actually acquired for the target candidate. In one such example, area 300 shown in FIG. 3 may be roughly the size of the image that was acquired at the target candidate. In addition, area 300 may be the size of the difference image generated for the target candidate. The location of the target candidate within that image may then be determined using correlation as described above. An area known to be larger than the target candidate may then be used to determine a threshold on a target candidate-by-target candidate basis as described above. For example, as shown in FIG. 3, area 302 within area 300 may be used to determine the threshold for the target candidate. The threshold may then be applied to an area slightly larger than the area of the known DOI. For example, as shown in FIG. 3, area 304 within area 302 may be the area to which the threshold is applied, and area 304 may be slightly larger than the area of the known DOI. In one such example, the portion of the image used to determine the threshold may be about 64 pixels by about 64 pixels while the area to which the determined threshold is applied may be about 5 pixels by about 5 pixels, depending on the size of the known DOI. Reducing the size of the difference image to which the threshold is applied reduces the possibility that noise in the image will be mistakenly identified as a potential DOI. In addition, using such a substantially small area as the care area to which the threshold is applied allows the use of a substantially low threshold without detecting overwhelming nuisance defects. For this reason, the care area used in this embodiment is referred as a micro care area or MCA. In contrast, many currently used inspection methods that use relatively low thresholds for substantially sensitive inspection detect huge amounts of nuisance defects that have to then be separated from the DOIs.

In one embodiment, the method includes selecting one or more characteristics of the target, selecting the one or more detection parameters, and determining one or more parameters of a care area such that defects other than the known DOI are not detected in the target candidates (e.g., only locations in which the known DOI likely occur are inspected). For example, the care areas may be reduced to include areas only for known DOIs and to substantially exclude the areas that do not contain known DOIs and only contain nuisance defects. In particular, the care areas can be defined around the locations where known DOI may occur. Therefore, noise outside of the care areas can be completely ignored. In addition, since the image of the target or a template can be used to find substantially exact locations of the target candidates, the care areas can be made substantially small. The care areas used in the embodiments described herein may also be substantially smaller than other currently used care areas since other methods do not have a mechanism to locate target candidates substantially accurately. The more accurate the target candidate locations can be determined, the smaller the care area that can be used and the less nuisance defects will be detected. In addition, the embodiments described herein can detect systematic defects by refining care area locations that originate from design data.

Although the embodiments are described herein with respect to searching for target candidates and detecting the known DOI in the target candidates, it is to be understood that the embodiments described herein can be used to search more than one type of target candidate and to detect DOI in more than one type of target candidate. For example, there may be multiple types of bridge defects on a wafer, or the same type of bridge may occur in different wafer structures. These bridges can be treated as different types of targets. The embodiments described herein may include using the information about these types of targets to search an entire die for any other instances of the target candidates. MCAs are defined around these target candidates and their locations are refined during inspection. Defect detection may be performed for each instance of the target candidates. In this manner, the embodiments described herein may be used to inspect target candidates across an entire wafer.

In one embodiment, none of the steps of the method are performed using design data for the wafer or the other wafer. In other words, design data for the wafer or the other wafer is not required for any step of the method. Therefore, the embodiments described herein are advantageous in that they do not require design data. Instead, inspection images other than GDS information are used. As such, GDS availability is not an issue. In contrast, methods that use hot spots require design data in order to be performed. Such methods sometimes also need support from someone (e.g., a customer) with design knowledge. However, since the embodiments described herein do not require any design data, any user can perform the inspection, which is a significant advantage particularly since the design data may not be available in all instances.

In one embodiment, each step of the method independently may use design data for the wafer or the other wafer. For example, the embodiments described herein can work with information provided from design data. For example, a design engineer may indicate a wafer structure that is prone to a bridge defect and would like to monitor the location. Target information can be generated, and a search can be performed in a die to find all target candidates having the same pattern as the target. Defect detection can be performed in these target candidates to find other targets on this wafer or other wafers. In another embodiment, design-based pattern search can be performed to find all target candidates on a die. The embodiment described herein can generate target information, skip the image-based search and perform defect detection at these target candidates.

The embodiments described herein may also be performed as design-based inspection. For example, all target candidate locations can be used as hot spot locations. Design-based inspection creates relatively small care areas around hot spots and performs patch-to-design alignment to refine care area locations. Then, defect detection is performed at hot spots.

In another embodiment, signals in the images of the target candidates corresponding to the known DOI are approximately equal to or weaker than signals corresponding to nuisance defects on the wafer. For example, a regular inspection may involve performing defect detection in inspection care areas that cover most of the area of the die. In situations in which signals for DOIs are much weaker than false (nuisance) defects, overwhelming false defects can be detected by existing approaches. For example, in order to detect defects with relatively weak signals, a substantially sensitive inspection may be performed, which also detects many nuisance defects. The nuisance count may be more than 99% of the total detected events. It is substantially difficult to find DOI among such massive amounts of nuisance defects. For example, feature vectors and defect attributes may be computed for each defect from images and used in defect classification. However, sometimes, the DOIs cannot be separated from nuisance defects because these two types of events can occupy the same areas in feature vector and attribute space. Therefore, extra information must be used to solve this problem. Furthermore, if a less sensitive inspection is used, the nuisance rate can be significantly reduced but DOI may also be lost (i.e., undetected).

In contrast, the embodiments described herein suppress huge amounts of nuisance defects. For example, the embodiments described herein use information that targets on specific DOI and is very relevant for defect detection. Classification approaches remove nuisance defects after nuisance events are detected. The embodiments described herein attempt to prevent nuisance events from being detected. More specifically, the embodiments described herein allow a highly sensitive inspection to be run while controlling the nuisance defect count by inspecting the wafer in areas (i.e., the target candidates) in which the known DOI will likely appear. In other words, using substantially accurate defect location information as described herein is a major contributor to nuisance suppression. In this manner, the embodiments described herein can achieve significant nuisance defect suppression for known DOIs with relatively weak signals in repeating structures. Thus, the embodiments described herein can detect DOIs and suppress nuisance defects more accurately.

The embodiments described herein may be complementary to any other inspection that may also be used to inspect the wafer. For example, in another embodiment, the method includes acquiring other images for the wafer or the other wafer and using the other images to detect other defects on the wafer or the other wafer. In one such example, for other areas, a regular inspection may be setup and run as usual to detect randomly-distributed defects and the embodiments described herein may be run to detect systematic defects with relatively weak signals. In addition, detecting the known DOIs as described herein and regular inspection can be performed in one test thereby providing significant throughput advantages. For example, the embodiments described herein may be used to detect known DOIs with relatively weak signals and can be run in parallel with any general inspection approach.

The embodiments described herein may also be used for specific nuisance defect removal. For example, the embodiments described herein may be performed as described herein but instead of being performed for a known DOI, the embodiments can be performed for a known systematic nuisance defect. The known nuisance defects can be defined as removal targets. The embodiments described herein can search removal target candidates on a die and not perform defect detection at removal target candidates. Thus, this type of nuisance defect will not be detected.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method detects the defects, the method may include storing information about the detected defects in a storage medium.

Figure 4:
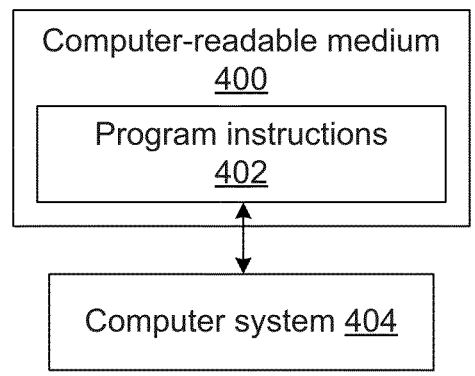
FIG. 4 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for detecting defects on a wafer. One such embodiment is shown in FIG. 4. In particular, as shown in FIG. 4, non-transitory computer-readable medium 400 includes program instructions 402 executable on computer system 404. The computer-implemented method includes the steps of the method described above. The computer-implemented method for which the program instructions are executable may include any other step(s) described herein.

Program instructions 402 implementing methods such as those described herein may be stored on computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 5:
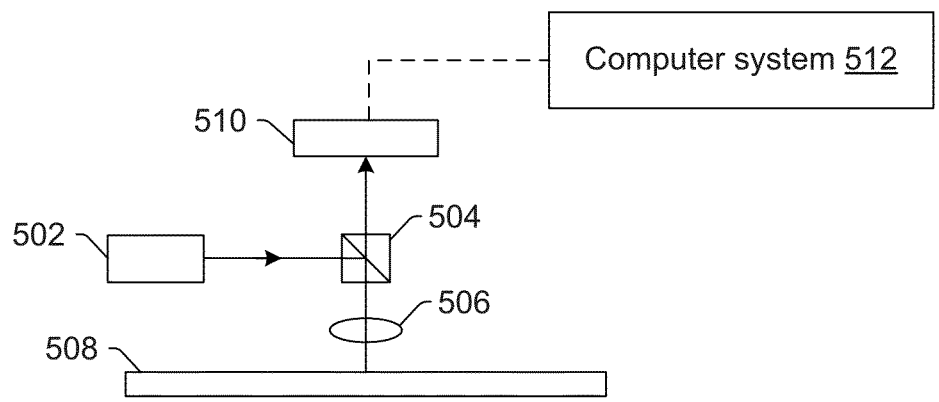
FIG. 5 is a schematic diagram illustrating a side view of one embodiment of a system configured to detect defects on a wafer.

Another embodiment relates to a system configured to detect defects on a wafer. One embodiment of such a system is shown in FIG. 5. The system includes an inspection subsystem configured to acquire information for a target on a wafer. The inspection subsystem may include any suitable inspection subsystem such as an e-beam inspection subsystem. Examples of suitable e-beam inspection subsystems include those that are included in commercially available e-beam inspection tools such as the eSxxx tools from KLA-Tencor, Milpitas, Calif. Alternatively, the inspection subsystem may include an optical inspection subsystem, which may have a configuration as described herein.

The target includes a POI formed on the wafer and a known DOI occurring proximate to or in the POI. The target may be further configured as described herein. The information includes an image of the target on the wafer acquired by imaging the target on the wafer. The image of the target may include any suitable data, image data, signals or image signals. The inspection subsystem may image the target on the wafer in any suitable manner. The information for the target may include any other target information described herein.

The inspection subsystem is also configured to search for target candidates on the wafer or another wafer. The target candidates include the POI. The target candidates may be configured as described herein. As shown in FIG. 5, the inspection subsystem includes light source 502. Light source 502 may include any suitable light source known in the art such as a laser. Light source 502 is configured to direct light to beam splitter 504, which is configured to reflect the light from light source 502 to refractive optical element 506. Refractive optical element 506 is configured to focus light from beam splitter 504 to wafer 508. Beam splitter 504 may include any suitable beam splitter such as a 50/50 beam splitter. Refractive optical element 506 may include any suitable refractive optical element, and although refractive optical element 506 is shown in FIG. 5 as a single refractive optical element, it may be replaced with one or more refractive optical elements and/or one or more reflective optical elements.

Light source 502, beam splitter 504, and refractive optical element 506 may, therefore, form an illumination subsystem for the inspection subsystem. The illumination subsystem may include any other suitable elements (not shown in FIG. 5) such as one or more polarizing components and one or more filters such as spectral filters. As shown in FIG. 5, the light source, beam splitter, and refractive optical element are configured such that the light is directed to the wafer at a normal or substantially normal angle of incidence. However, the light may be directed to the wafer at any other suitable angle of incidence. The inspection subsystem may be configured to scan the light over the wafer in any suitable manner.

Light reflected from wafer 508 may be collected by refractive optical element 506 and may be directed through beam splitter 504 to detector 510. Therefore, the refractive optical element, the beam splitter, and the detector may form a detection subsystem of the inspection subsystem. The detector may include any suitable imaging detector known in the art such as a charge coupled device (CCD). The detection subsystem may also include one or more additional components (not shown in FIG. 5) such as one or more polarizing components, one or more spatial filters, one or more spectral filters, and the like. Detector 510 is configured to generate an image that is responsive to the reflected light detected by the detector.

The system also includes computer system 512 configured to detect the known DOI in the target candidates by identifying potential DOI locations in images of the target candidates and applying one or more detection parameters to images of the potential DOI locations. The computer system may identify the locations and apply the one or more detection parameters as described further herein. In addition, the computer system may be configured to perform any other step(s) described herein. Images generated by the detector may be provided to computer system 512. For example, the computer system may be coupled to the detector (e.g., by one or more transmission media shown by the dashed lines in FIG. 5, which may include any suitable transmission media known in the art) such that the computer system may receive the images generated by the detector. The computer system may be coupled to the detector in any suitable manner. The computer system may be further configured as described herein. The inspection subsystem may also be further configured as described herein. Furthermore, the system may be further configured as described herein.

It is noted that FIG. 5 is provided herein to generally illustrate one configuration of an inspection subsystem that may be included in the system embodiments described herein. Obviously, the inspection subsystem configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 28XX, 29XX, and Puma 9XXX series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the inspection subsystem is described above as a bright field (BF) inspection subsystem, it is to be understood that the inspection subsystem may also or alternatively be configured as a dark field (DF) inspection subsystem (i.e., an inspection subsystem configured to detect defects using scattered light).

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
    acquiring information for a target on a wafer, wherein the target comprises a pattern of interest formed on the wafer and a known defect of interest having a location that is known and unique relative to a location of the pattern of interest, and wherein the information comprises an image of the target on the wafer acquired by imaging the target on the wafer, the location of the pattern of interest on the wafer, and the location of the known defect of interest relative to the pattern of interest;
    searching for target candidates on the wafer or on another wafer, wherein the target candidates comprise the pattern of interest; and
    detecting the known defect of interest in the target candidates by identifying potential defect of interest locations in images of the target candidates and applying one or more detection parameters to images of the potential defect of interest locations, wherein said detecting is performed using a computer system.

2. A non-transitory computer-readable medium, storing program instructions executable on a computer system for performing a computer-implemented method for detecting defects on a wafer, wherein the computer-implemented method comprises:
    acquiring information for a target on a wafer, wherein the target comprises a pattern of interest formed on the wafer and a known defect of interest having a location that is known and unique relative to a location of the pattern of interest, and wherein the information comprises an image of the target on the wafer acquired by imaging the target on the wafer, the location of the pattern of interest on the wafer, and the location of the known defect of interest relative to the pattern of interest;
    searching for target candidates on the wafer or on another wafer, wherein the target candidates comprise the pattern of interest; and
    detecting the known defect of interest in the target candidates by identifying potential defect of interest locations in images of the target candidates and applying one or more detection parameters to images of the potential defect of interest locations.

3. A system configured to detect defects on a wafer, comprising:
    an inspection subsystem configured to acquire information for a target on a wafer, wherein the target comprises a pattern of interest formed on the wafer and a known defect of interest having a location that is known and unique relative to a location of the pattern of interest, and wherein the information comprises an image of the target on the wafer acquired by imaging the target on the wafer, the location of the pattern of interest on the wafer, and the location of the known defect of interest relative to the pattern of interest;
    wherein the inspection subsystem is further configured to search for target candidates on the wafer or on another wafer, wherein the target candidates comprise the pattern of interest; and
    a computer system configured to detect the known defect of interest in the target candidates by identifying potential defect of interest locations in images of the target candidates and applying one or more detection parameters to images of the potential defect of interest locations.

4. The system of claim 3, wherein the inspection subsystem is further configured to acquire the information and search for the target candidates without using design data for the wafer or the other water, and wherein the computer system is further configured to detect the known defect of interest without using the design data for the water or the other wafer.

5. The system of claim 3, wherein the computer system is further configured to acquire the information by specifying size, shape and location of care areas, size, shape and location of templates, and area where one or more characteristics are determined in the images to which the one or more detection parameters are applied.

6. The system of claim 3, wherein the pattern of interest has a width and a height that are shorter than a width and a height, respectively, of dies formed on the wafer and the other wafer.

7. The system of claim 3, wherein the computer system is further configured to generate micro care areas to cover one or more of the potential defect of interest locations.

8. The system of claim 3, wherein the computer system is further configured to determine a care area location by correlating a template image for the pattern of interest and the images used for detecting the known defect of interest.

9. The system of claim 3, wherein the computer system is further configured to select one or more characteristics of the target, select the one or more detection parameters, and determine one or more parameters of a care area such that defects other than the known defect of interest are not detected in the target candidates.

10. The system of claim 3, wherein the inspection subsystem is further configured to acquire other images for the wafer or the other wafer, and wherein the computer system is further configured to detect other defects on the wafer or the other wafer using the other images.

11. The system of claim 3, wherein the images to which the one or more detection parameters are applied comprise images generated using a reference image and a test image, and wherein the reference image is a template for the pattern of interest.

12. The system of claim 3, wherein the computer system is further configured to detect the known defect of interest by providing the information for the target to a defect detection module in order to identify the potential defect of interest locations accurately.

13. The system of claim 3, wherein the computer system is further configured to detect the known defect of interest by identifying the potential defect of interest locations in the images of the target candidates by correlating a template obtained during setup and the images of the target candidates obtained during detection of the known defect of interest by the computer system.

14. The system of claim 3, wherein the computer system is further configured to determine the one or more detection parameters based on the information for the target.

15. The system of claim 3, wherein the computer system is further configured to determine the one or more detection parameters separately for each type of the target candidates based on images for each type of the target candidates, respectively.

16. The system of claim 3, wherein applying the one or more detection parameters comprises generating difference images using the images of the potential defect of interest locations and a reference image and applying a threshold to signals in the difference images.

17. The system of claim 3, wherein the computer system is further configured to determine one or more characteristics of a difference image for the potential defect of interest locations, and wherein applying the one or more detection parameters comprises applying a threshold to one or more values of the one or more characteristics of the difference image.

18. The system of claim 3, wherein the images of the potential defect of interest locations to which the one or more detection parameters are applied are images of care areas surrounding the potential defect of interest locations, and wherein the care areas are determined based on a size of the known defect of interest having the location that is known and unique relative to the location of the pattern of interest.

19. The system of claim 3, wherein the known defect of interest is a defect that occurs repeatedly in certain patterns on the wafer.

20. The system of claim 3, wherein the known defect of interest is a systematic defect.

21. The system of claim 3, wherein the inspection subsystem is further configured as an electron beam inspection subsystem.

22. The system of claim 3, wherein the inspection subsystem comprises an imaging detector configured to detect light reflected from the wafer and to generate an image that is responsive to the reflected light detected by the detector.

23. The system of claim 3, wherein the inspection subsystem is further configured as a bright field inspection subsystem.

* * * * *